United States Patent
Wu et al.

(10) Patent No.: US 12,048,741 B2
(45) Date of Patent: Jul. 30, 2024

(54) RECOMBINANT HOST CELL WITH HETEROLOGOUS NUCLEIC ACIDS ENCODING SHREK PROTEINS

(71) Applicant: George Mason University, Fairfax, VA (US)

(72) Inventors: Yuntao Wu, Manassas, VA (US); Deemah Dabbagh, Fairfax, VA (US); Sijia He, Manassas, VA (US); Brian Hetrick, Woodbridge, VA (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 507 days.

(21) Appl. No.: 17/031,082

(22) Filed: Sep. 24, 2020

(65) Prior Publication Data

US 2021/0093709 A1     Apr. 1, 2021

Related U.S. Application Data

(60) Provisional application No. 63/061,683, filed on Aug. 5, 2020, provisional application No. 63/008,054, filed on Apr. 10, 2020, provisional application No. 62/906,890, filed on Sep. 27, 2019.

(51) Int. Cl.
    *A61K 39/12*     (2006.01)
    *A61K 38/16*     (2006.01)
    *C12N 15/86*     (2006.01)
    *A61K 39/00*     (2006.01)

(52) U.S. Cl.
    CPC .......... *A61K 39/12* (2013.01); *A61K 38/162* (2013.01); *C12N 15/86* (2013.01); *A61K 2039/507* (2013.01); *A61K 2039/5254* (2013.01)

(58) Field of Classification Search
None
See application file for complete search history.

(56) References Cited

U.S. PATENT DOCUMENTS

| | | | | |
|---|---|---|---|---|
| 11,116,833 | B2 * | 9/2021 | Wu | ...................... C12N 5/0636 |
| 11,382,967 | B2 * | 7/2022 | Wu | .......................... C12N 7/00 |
| 2021/0093709 | A1 * | 4/2021 | Wu | ........................ A61K 39/12 |

OTHER PUBLICATIONS

Fauci et al. (Annals of Internal Medicine. 1996; 124: 654-663).*
Murakami et al. (Viruses. 2021; 13: 1935).*
Fu et al. (PNAS. 2020; 117 (17): 9537-9545).*
He et al. (Viruses. 2021; 13: 46).*
Burnie (Retrovirology. 2022; 19: 9).*
Zaongo et al. (Viruses. 2023; 15: 2197).*

* cited by examiner

*Primary Examiner* — Shanon A. Foley
(74) *Attorney, Agent, or Firm* — WC&F IP

(57) ABSTRACT

Recombinant viruses include one or more SHREK proteins and are thereby rendered non-infective and can be safely used in vaccines, e.g. to treat or prevent infections and to eliminate e.g. latent virus reservoirs.

13 Claims, 11 Drawing Sheets

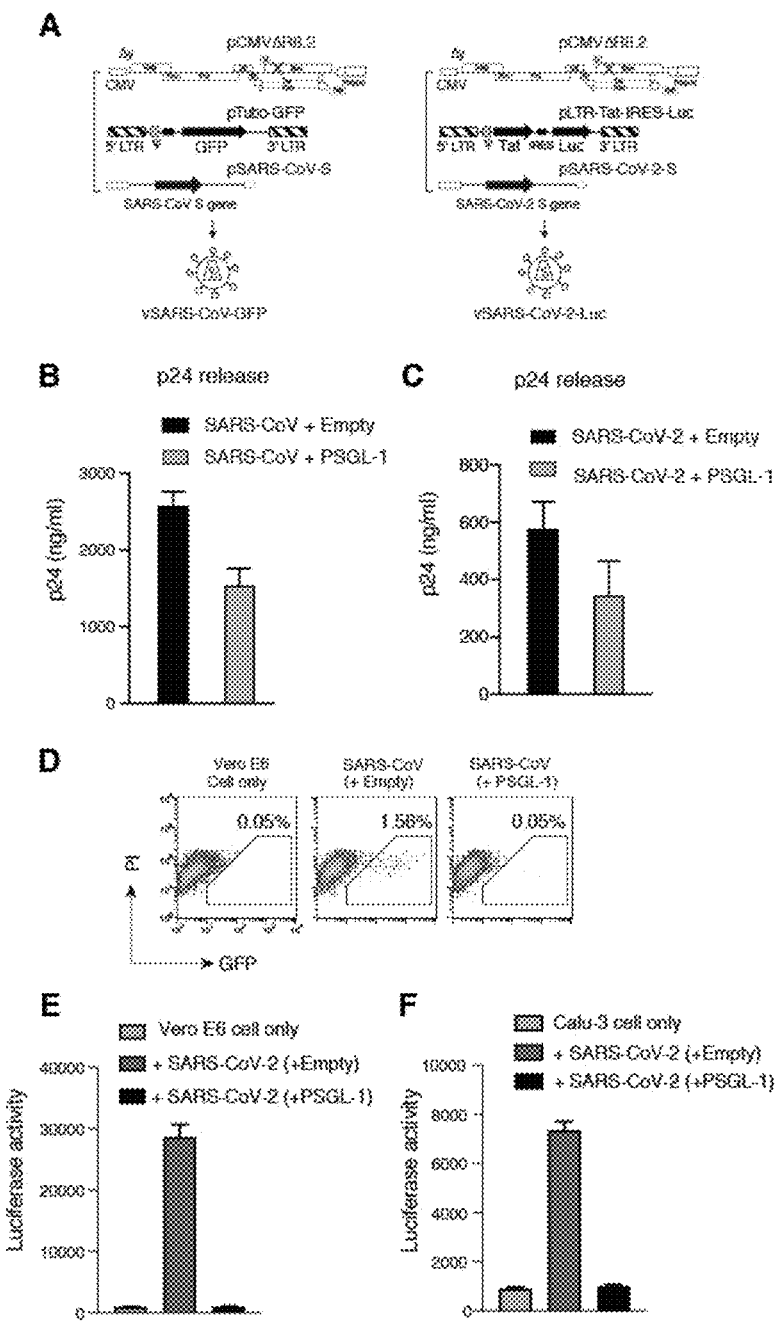
Figure 1A-F

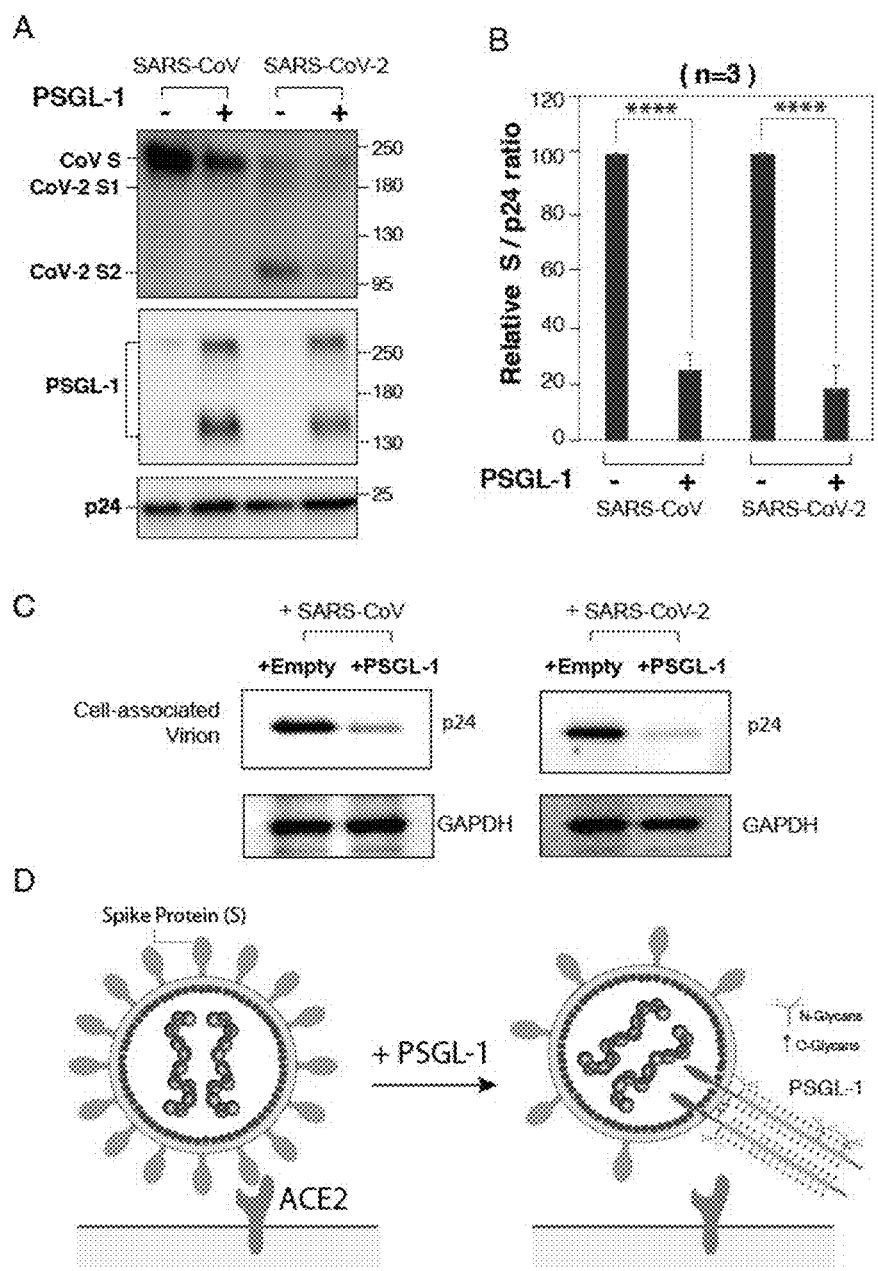
Figure 2A-D

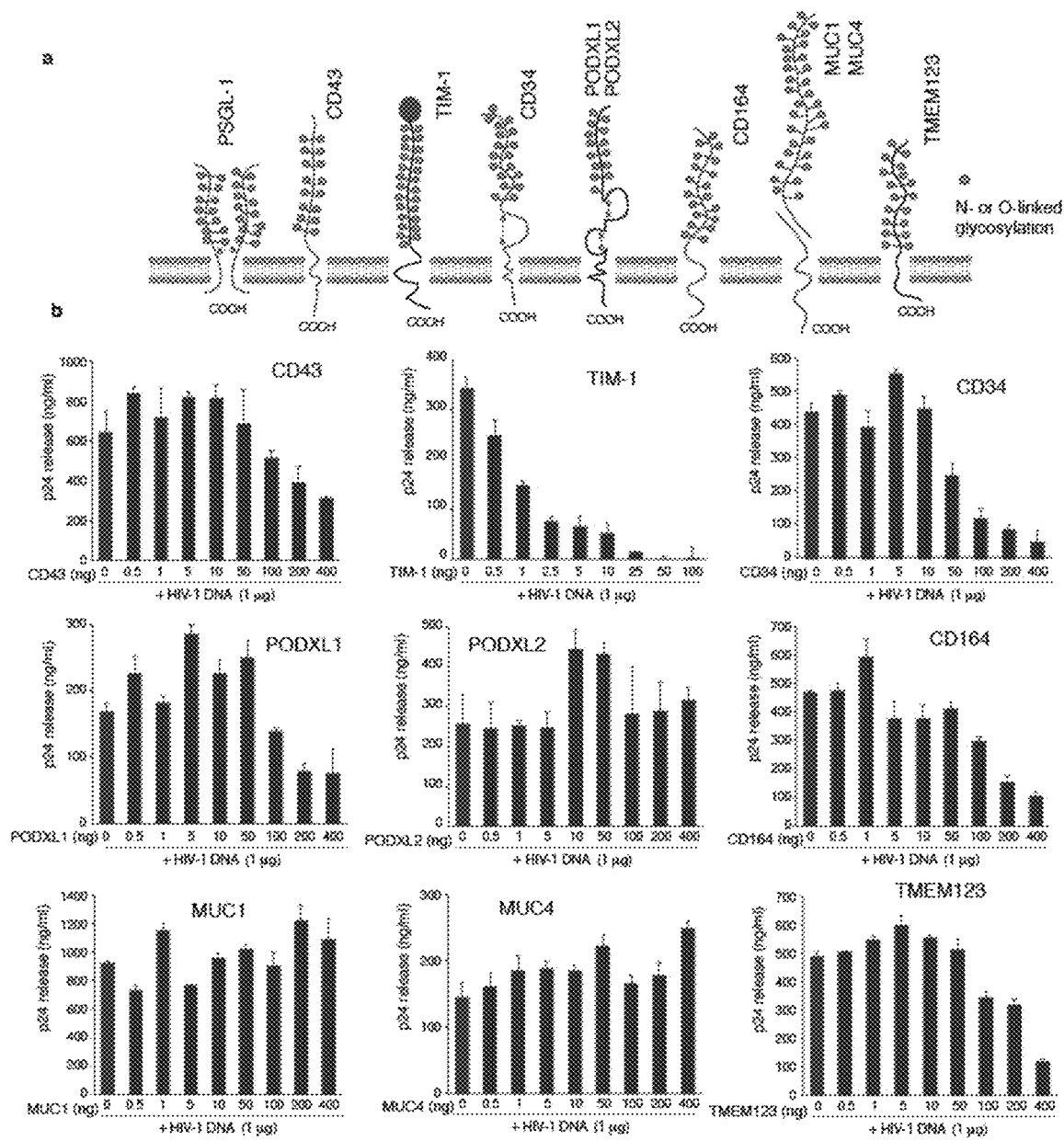
Figure 3A-B

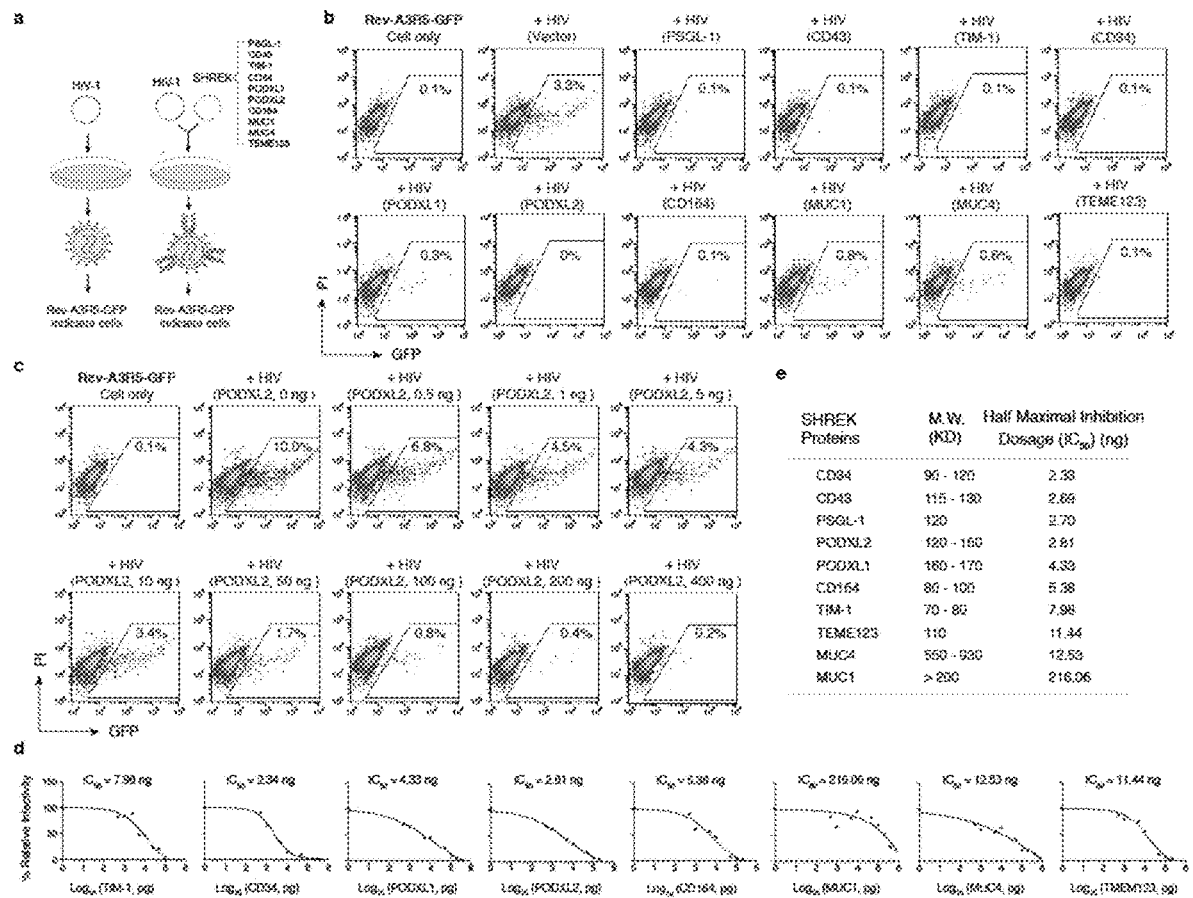
Figure 4A-E

Figure 5A
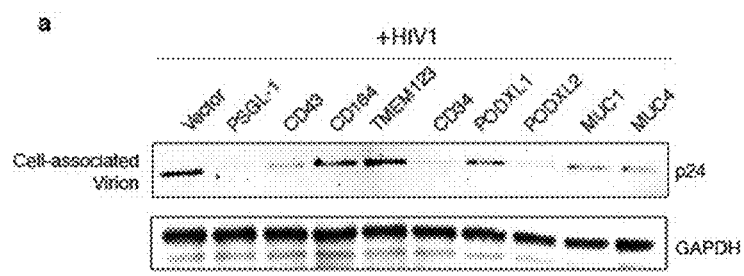
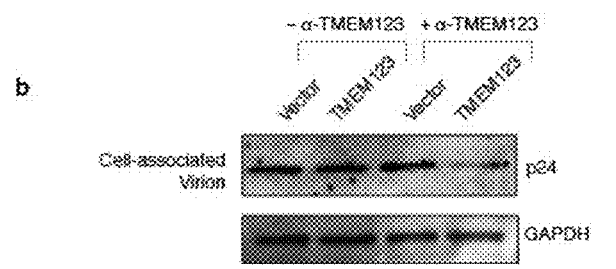
Figure 5B

Figure 6A  Figure 6B
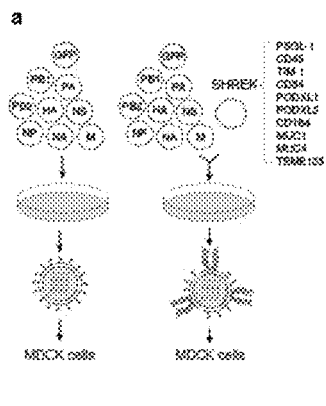
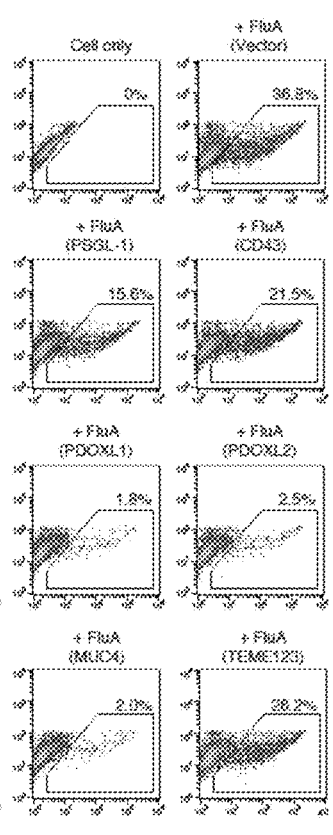
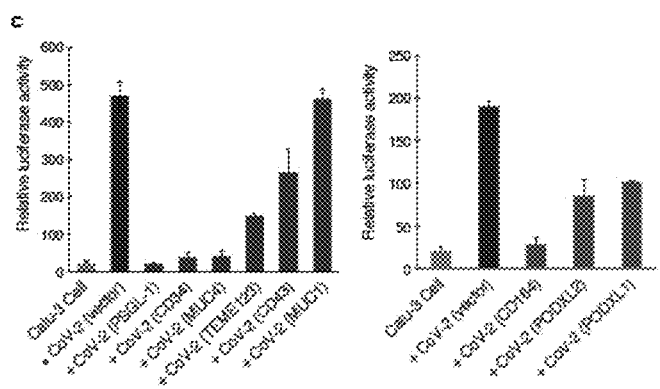
Figure 6C

Figure 7A
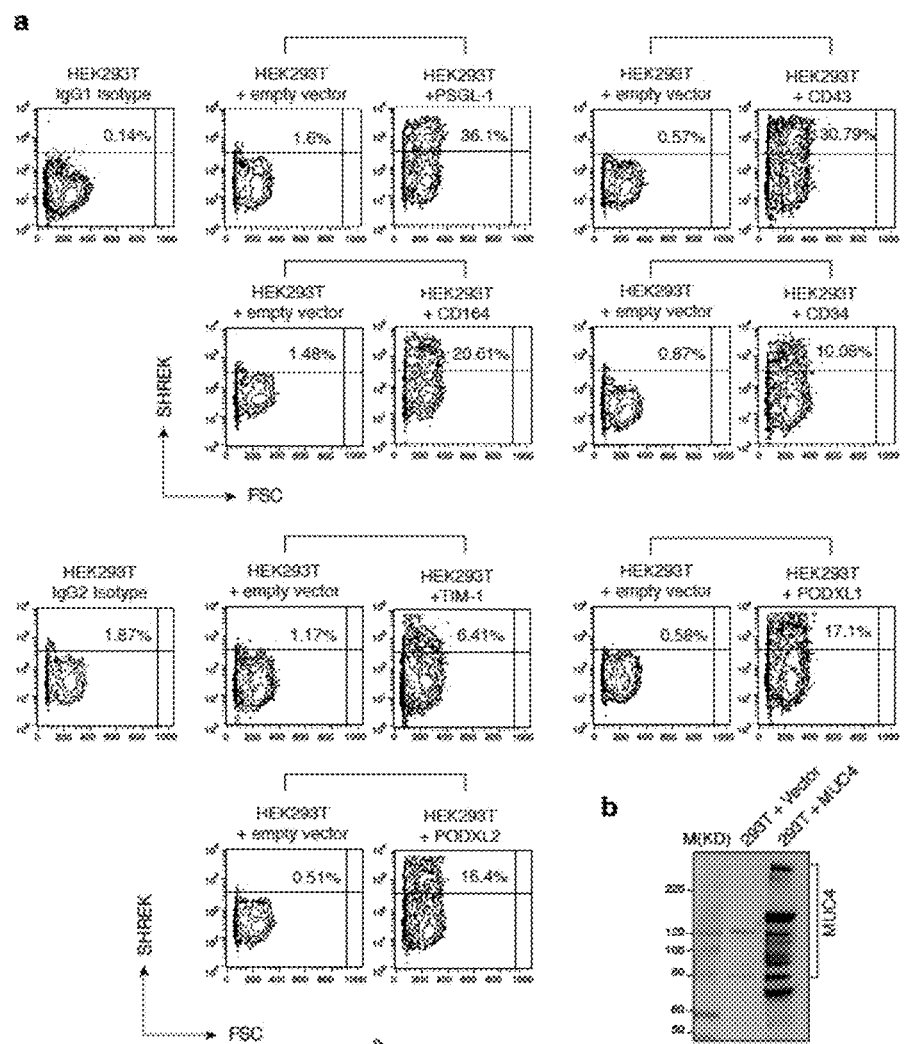
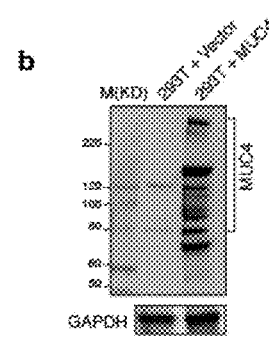
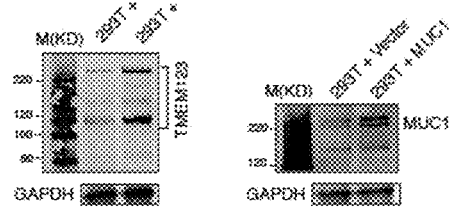
Figure 7B

RECOMBINANT HOST CELL WITH HETEROLOGOUS NUCLEIC ACIDS ENCODING SHREK PROTEINS

CROSS-REFERENCE TO RELATED APPLICATIONS

This application claims benefit of U.S. provisional patent application 62/906,890 filed Sep. 27, 2019, U.S. provisional patent application 63/008,054 filed Apr. 10, 2020 and U.S. provisional patent application 63/061,683 filed Aug. 5, 2020.

STATEMENT OF FEDERALLY SPONSORED RESEARCH AND DEVELOPMENT

This invention was made with government support under grant number 1R01AI148012 awarded by the National Institutes of Health. The government has certain rights in the invention.

BACKGROUND OF THE INVENTION

Field of the Invention

The invention generally relates to methods of preparing and using anti-viral agents. In particular, the invention provides i) viruses which, when assembled, include one or more SHREK proteins and are thereby rendered non-infective and hence attenuated, and can be safely used in vaccines, e.g. to treat or prevent infections and to eliminate latent virus reservoirs.

Description of Related Art

Disease caused by viruses have devastating health consequences. For example, the ongoing coronavirus disease 2019 (COVID-19) is a global pandemic afflicting more than 10 million people in over 200 countries and territories, resulting in more than 500,000 deaths as of Jun. 30, 2020. Currently, there are no effective treatments or vaccines for COVID-19. As another example, since the discovery of HIV in the early 1980s, the virus has spread world-wide, and remains a pandemic disease of significant public health implications. Significant medical progress has been made in combating HIV infection, transmission, and disease progression by the development of antiretroviral therapy (ART) drugs. However, ART must be taken for the entire lifetime of the affected patients to keep viral replication levels below detectable levels, and no vaccine is available.

Understanding virus-host interactions is critical for developing novel therapeutics and vaccines.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

This disclosure includes the identification of a group of mucin-like glycoproteins that are normally found on the surface of cells and which function as restriction factors of many viruses. Based on common characteristics shared among these proteins, they are referred to herein as the "SHREK" (Surface-Hinged, Rigidly-Extended Killer) family of proteins of virion inactivators. In some aspects, when expressed in virion producing cells, the SHREK proteins are incorporated into virions during viral assembly, thereby attenuating the virus and preventing it from being infective. In other aspects, the SHREK proteins or portions thereof are incorporated into antibody-SHREK conjugates. The antibody portion of the conjugate targets and binds to viral particles, and the SHREK portion of the conjugate insures that the virus particle is then inactive and cannot infect host cells.

It is an object of this invention to provide an attenuated virus comprising a SHREK protein, with the caveat that if the attenuated virus is a lentivirus or an influenza virus, then the SHREK protein is not PSGL-1 or CD43. In some aspects, the attenuated virus is an enveloped virus. In further aspects, the enveloped virus is a coronavirus, a lentivirus, a Hepadnavirus or an influenza virus. In additional aspects, the coronavirus is SARS-CoV-2. In yet further aspects, the lentivirus is HIV-1 or HIV-2. In other aspects, the Hepadnavirus is Hepatitis B (HBV). In other aspects, the SHREK protein is PSGL-1, CD43, TMEM123, CD164, Tim-1, CD34, PODXL2, CD45, CD44, Madcam1, glycam1, Cd68, CD148, CX3CL1, CD107a, CD99, or CD7.

Also provided is a method of eliciting an immune response to a virus in a subject in need thereof, comprising administering to the subject an amount of an attenuated virus comprising a SHREK protein, that is sufficient to elicit the immune response to the virus. In some aspects, the immune response is protective.

Also provided is a recombinant host cell comprising one or more vectors comprising nucleic acid sequences encoding a SHREK protein and a viral genome. In some aspects, the host cell is a mammalian cell.

Also provided is a pharmaceutical composition comprising a plurality of attenuated viruses comprising a SHREK protein, a pharmaceutically acceptable carrier; and, optionally, one or more adjuvants. In some aspects, the pharmaceutical composition is a vaccine.

Also provided is a method of producing attenuated virions, comprising I) introducing into a host cell a nucleic acid sequence encoding a SHREK protein, and one or more nucleic acid sequences encoding a viral genome; II) culturing the host cell in a culture medium under conditions that permit i) over-expression of the SHREK protein from the nucleic acid sequence encoding a SHREK protein and over-expression of viral proteins and viral nucleic acids from the one or more nucleic acid sequences encoding a viral genome, and ii) assembly of the viral proteins and viral nucleic acids into attenuated virions comprising the SHREK protein; and III) recovering the attenuated virions from the culture medium.

BRIEF DESCRIPTION OF THE DRAWINGS

FIG. 1A-F. PSGL-1 inactivates the infectivity of SARS-CoV and SARS-CoV2 pseudoviruses. A) Schematic of the assembly of lentiviral particles pseudotyped with the S proteins of SARS-CoV and SARS-CoV-2. B and C) Effects of PSGL-1 on viral release. A PSGL-1 expression vector or control empty vector was cotransfected with the lentivirus packaging construct and a GFP or luciferase reporter plasmid, and viral release was quantified at 72 hours post-transfection by HIV-1 p24 ELISA. D) The infectivity of the SARS-CoV pseudotyped virions was quantified by infecting Vero E6 cells and measuring GFP expression at 72 hours post-infection. The percentages of GFP+ cells are shown. E and F) The infectivity of the SARS-CoV-2 pseudotyped virions was quantified by infecting Vero E6 (E) and Calu-3 cells (F). Luciferase activity in infected cells was quantified at 72 hours post infection.

FIG. 2A-D. PSGL-1 inhibits virion incorporation of SARS-CoV and SARS-CoV-2 S proteins and blocks virus attachment to target cells. A) PSGL-1 inhibits virion incorporation of S proteins. Virions were produced from HEK293T cells cotransfected with HIV-1 pNL4-3/KFS DNA, the vector expressing either the SARS-CoV or the SARS-CoV-2 S protein in the presence of PSGL-1 or an empty control vector. Virion proteins were analyzed by western blotting using antibodies against SARS-CoV S proteins (GeneTex), PSGL-1 (KPL-1 clone), or HIV-Ig to detect CA protein p24. B) The levels of SARS-CoV or SARS-CoV-2 S proteins in virions were quantified and normalized to viral p24 and set to 100% in the absence of PSGL-1. Data shown are ±SD from three independent experiments. P values (two-tailed unpaired t-test): ****p<0.0001. C) PSGL-1 blocks virus attachment to target cells. An equal number of virions produced in the presence of a PSGL-1 vector or empty vector was assayed for attachment to target Vero E6 cells at 4° C. for 2 hours. Cells were extensively washed, and cell-associated virions were analyzed by western blot for HIV-1 p24. GAPDH was used as a loading control. D) Model for the antiviral activity of PSGL-1 against SARS-CoV and CoV-2 S proteins. Left panel; in the absence of PSGL-1 in the virus-producer cell, virions bearing S protein bind the ACE2 receptor and infect the target cell. Right panel; expression of PSGL-1 in the virus-producer cell results in diminished S protein incorporation, and PSGL-1 incorporation into virions sterically blocks virus binding to target cells.

FIGS. 3A and B. Effects of SHREK proteins on viral release. A, Schematic of shared structural features of SHREK proteins with extended and heavily glycosylated extracellular domains. B, Effects of SHREK proteins on virion release. HEK293T cells were cotransfected with HIV(NL4-3) DNA (1 µg) plus each individual SHREK protein expression vector (0.5 to 400 ng of DNA). Viral p24 release was quantified at 48 hours by ELISA.

FIG. 4A-E. SHREK proteins inactivate HIV-1 virion infectivity. A, Schematic of virion production in the presence of SHREK proteins in virus producer cells. B, HEK293T cells were cotransfected with HIV(NL4-3) DNA (1 µg) plus each individual SHREK protein (500 ng). Virions were harvested at 48 hours and normalized for p24, and viral infectivity was quantified by infecting Rev-A3R5-GFP indicator cells. HIV-1 replication was quantified by GFP expression. Shown are the percentages of GFP+ cells at 48 hours post infection. C, Dose-dependent inhibition of HIV-1 infectivity by PODXL2 (0.5 to 400 ng of DNA) was quantified using Rev-A3R5-GFP. D, the dose-dependent inhibition curve of HIV-1 infectivity by each individual SHREK protein was plotted using results from 3 independent experiments. E, the 50% inhibition dosage (IC50) for each SHREK protein was calculated.

FIGS. 5A and B. SHREK proteins block HIV-1 virion attachment to target cells. A, Viral particles were produced by cotransfecting HEK293T cells with HIV-1 NL4-3 DNA (1 µg) and each individual SHREK protein-expressing vector or an empty vector (500 ng). p24-normalized viral particles were then assayed for attachment to target HeLaJC.53 cells and analyzed by Western blot for cell-bound p24; B, Virions produced in the presence of the TMEM123 expression vector or the empty vector were assayed for attachment in the presence or absence of an anti-TMEM123 antibody.

FIG. 6A-C. SHREK proteins inactivate influenza A and SARS-CoV-2 virion infectivity. A, Influenza A-GFP reporter viruses were assembled by cotransfecting HEK293T cells with eight vectors expressing each of the segments of influenza A/WSN/33 (H1N1) (0.25 µg each), pHW-NA-GFP (ΔAT6) (1.5 µg), and each individual SHREK-expressing vector or an empty vector (0.5 µg). Viral particles were harvested at 48 hours and used to infect target MDCK cells. B, GFP+ cells were quantified by flow cytometry following infection for 24 hours. C, SARS-CoV-2-S-pseudotyped luciferase reporter lentivirus particles were assembled in HEK293T cells by cotransfecting pLTR-Tat-IRES-Luc (10 µg), pCMVΔR8.2 (7 µg), SARS-CoV-2 S (1 µg), and each individual SHREK-expressing vector or an empty vector (2 µg). Viral supernatants were harvested and normalized for p24, and viral infectivity was quantified by infecting Calu-3 cells. Luciferase activity was measured at 72 h post infection.

FIGS. 7A and B. Expression of SHREK proteins in HEK293T cells. A, HEK293T cells were transfected with 400 ng of either PSGL-1, CD43, CD164, CD34, TIM-1, PODXL1, or PODXL2. Expression of each protein was quantified at 48 hours by surface staining using antibodies against each of the indicated proteins. B, HEK293T cells were transfected with 400 ng of MUC1, MUC4, TMEM123, or an empty vector. Expression of each protein was measured by Western blot using antibodies against MUC1, MUC4 or TMEM123.

DETAILED DESCRIPTION

Figure 8A:
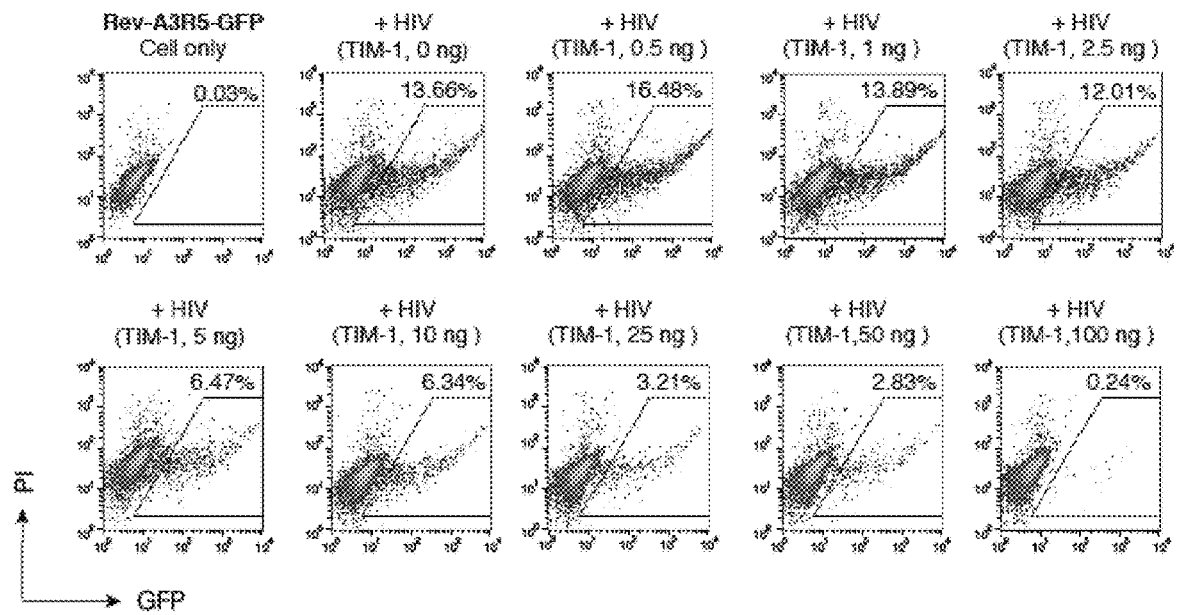
FIG. 8A-G. Dose-dependent inhibition of HIV-1. HIV-1 particles were produced in HEK293T cells by co-transfection of NL4-3 DNA (1 µg) plus an empty vector or the indicated doses of CD34. P24-normalized virions were used to infect Rev-A3R5-GFP cells. The percentage of GFP+ cells was quantified by flow cytometry at 72 hours post infection. Inhibition by: A, TIM-8A: B, CD34; C, PODXL1; D, CD164; E, MUC1; F, MUC4; G, TMEM123.
Figure 8B:
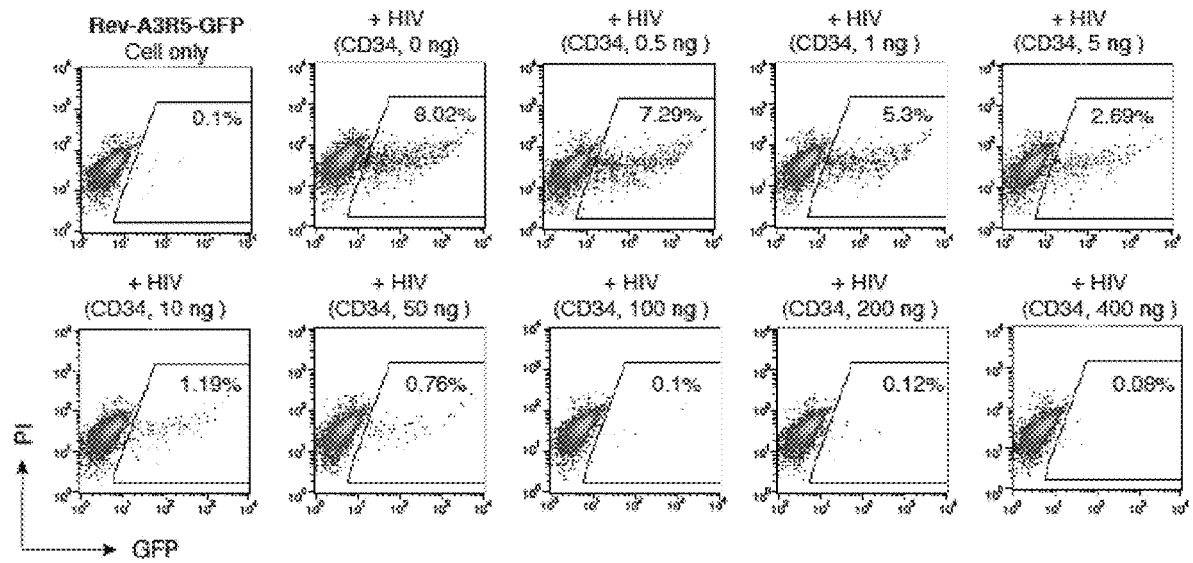
Figure 8C:
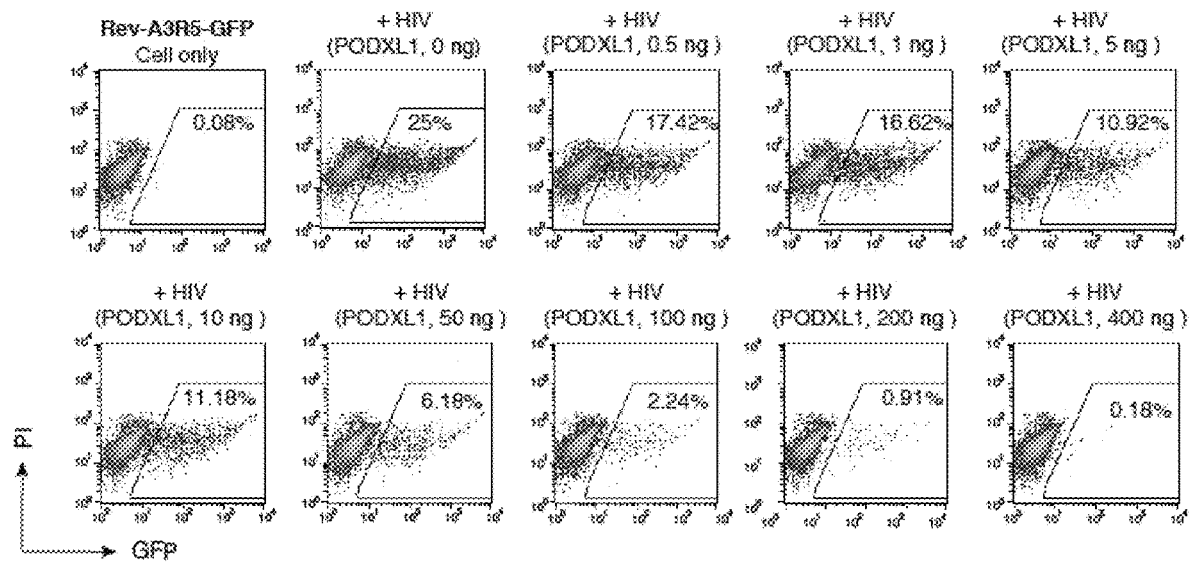
Figure 8D:
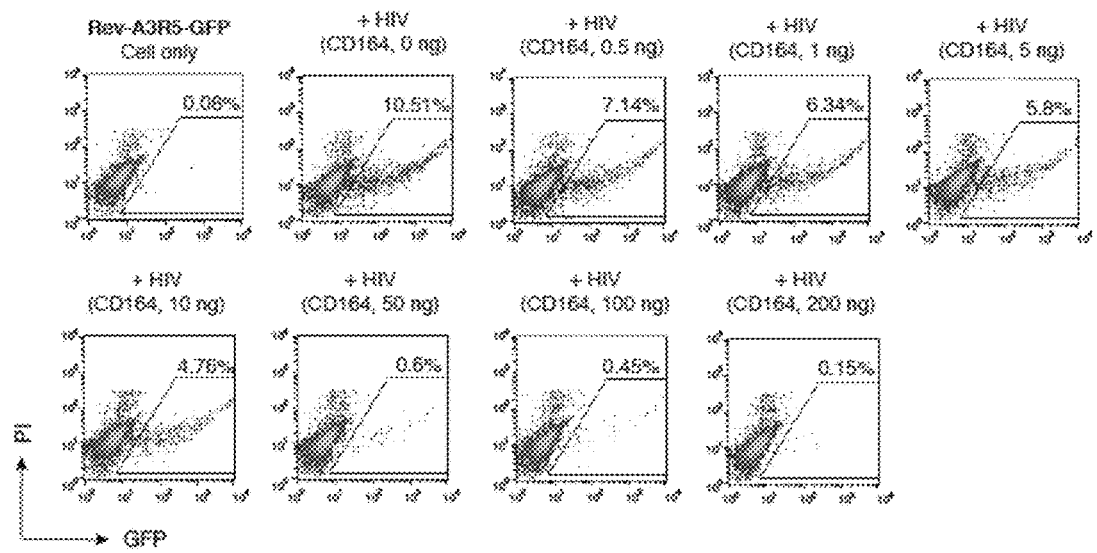
Figure 8E:
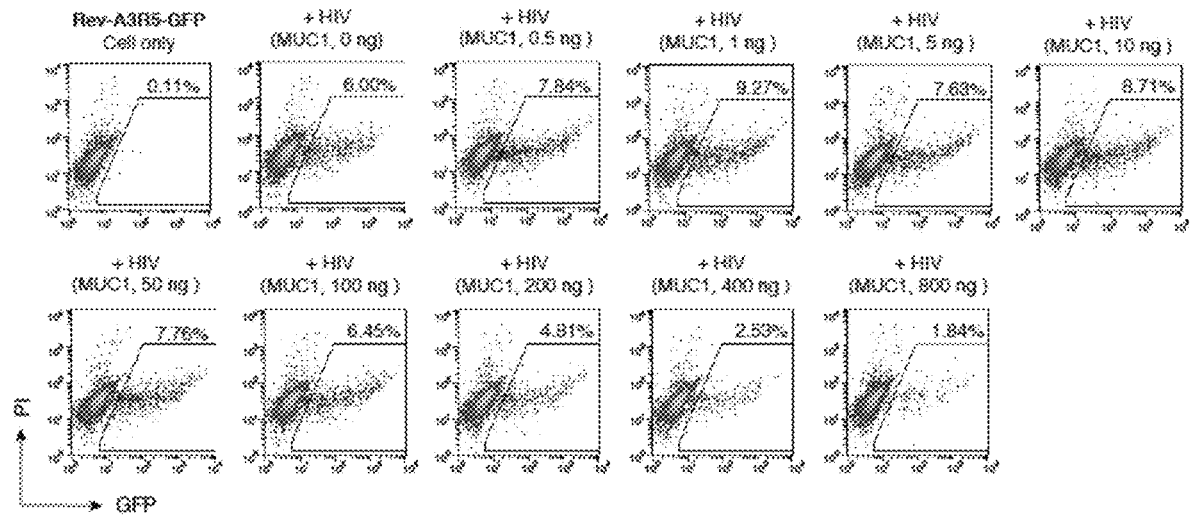
Figure 8F:
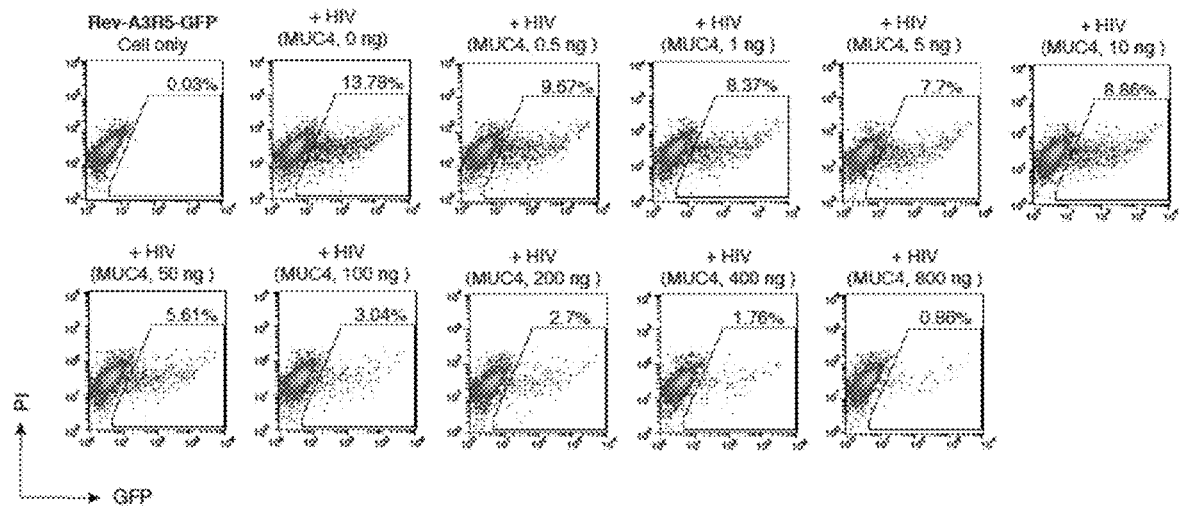
Figure 8G:
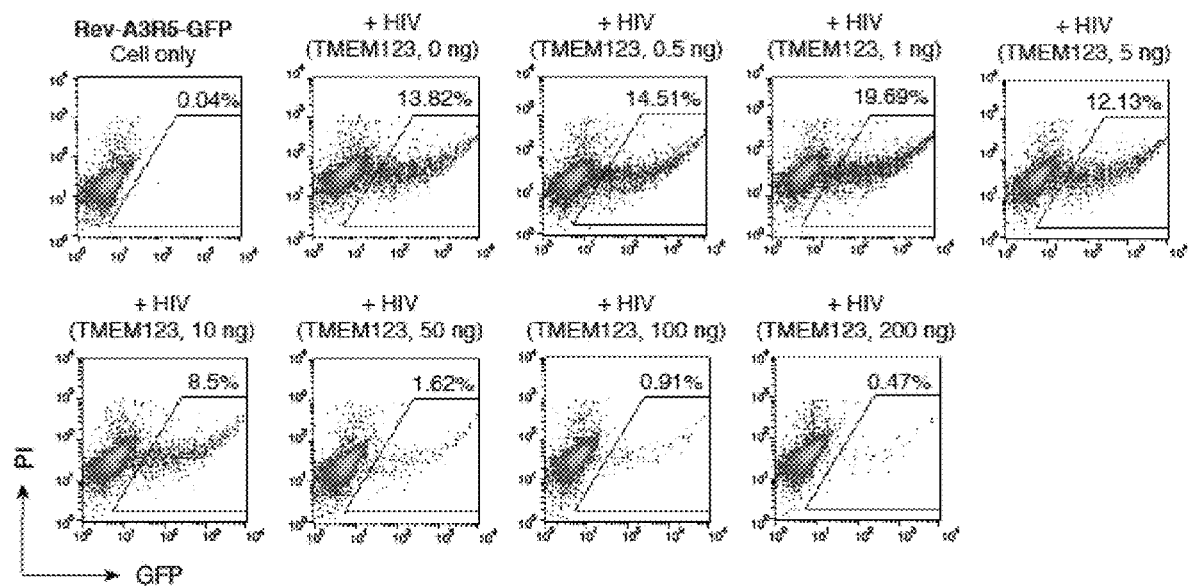

Antiviral agents usually work by inhibiting or reducing the ability of the virus to reproduce, typically by targeting and interfering with a specific step in the viral replication cycle. For the SHREK proteins disclosed herein, this intervention advantageously occurs at least at the earliest stage of the replication cycle: attachment of the virus to a target cell. For example, in order for HIV to successfully infect a target cell, the virus must first bind to the cell membrane. This initial interaction between the virus and host cell is essential for viral entry and subsequent replication. Members of the SHREK family of proteins, when present in a cell in which a virus is assembling, are incorporated into the virus. Once present in the virus, the SHREK proteins prevent infection of target cells by the virus. Without being bound by theory, it is believed that the antiviral activities of SHREKs are achieved through at least 3 different mechanisms: (1) blocking virion release from a cell that the virus has infected, thereby preventing transmission; (2) inhibition of virion incorporation of viral attachment proteins, thereby preventing attachment of the virus to target cells; and (3) virion incorporation of SHREK that blocks progeny virus attachment to target cells through steric hindrance. Whatever the mechanism, incorporation of at least one type of SHREK protein into a virion inhibits viral infectivity, thereby attenuating the virus and rendering it suitable for use in a vaccine.

In summary, there are at least 3 ways that SHREK can inactivate a virus particle: (1) assemble virus particles in the presence of SHREK. Virion incorporation of SHREK will inactivate virus infectivity; (2) Expression of SHREK in an infected cell, which will result in the cell releasing non-infectious virus particles; and (3) conjugating SHREK or the extracellular portion of SHREK proteins with the C-terminus of an antibody, which binds to the surface of a virus particle and prevents the binding and entry of viruses, thus precluding infectivity.

Accordingly, this disclosure encompasses the use of SHREK family proteins for developing new live-attenuated virus vaccines and new anti-viral therapies.

The SHREK Proteins

The acronym "SHREK" stands for "Surface-Hinged, Rigidly-Extended Killer". These proteins have the following characteristics: they have a mucin-like structure, exhibit heavy glycosylation, and possess large, rigid extracellular domains that extend relatively far from the cell surface. For example, previous studies have shown that some PSGL-1 extends nearly 50-60 nm from the cell surface, and the N-terminal extracellular domains are relatively rigid and heavily glycosylated.

Members of this family include but are not limited to: the newly identified restriction factor, PSGL-1 (P Selectin Glycoprotein Ligand 1, a mucin-like protein that serves as a model member of the SHREK family of proteins); mucin-like proteins such as CD43 (Sialophorin); TMEM123 (Transmembrane Protein 123); CD164 (Endolyn); Tim-1 (T-cell immunoglobulin and mucin domain 1); CD34; PODXL2 (Podocalyxin Like 2), TIM-4 (T-cell immunoglobulin and mucin domain 4), CD45, CD44, Madcam1, glycam1, Cd68, CD148, CX3CL1, CD107a, CD99, CD7, etc.

Any protein possessing the characteristics of the SHREK family of proteins may be used in the practice of the invention as described herein.

Viruses that are Targeted

The antiviral agents described herein are used against any enveloped virus. Several classes of enveloped viruses that contain human pathogens are recognized and include but are not limited to: DNA viruses (e.g. Herpesviruses, Poxviruses, Hepadnaviruses, Asfarviridae, Retroviruses such as Lentiviruses; Hepadnaviruses); RNA viruses (e.g. Flavivirus, Alphavirus, Togavirus, Coronavirus, Hepatitis, Orthomyxovirus, Paramyxovirus, Rhabdovirus, Bunyavirus and Filovirus);

Lentiviruses include but are not limited to: Bovine immunodeficiency virus, Caprine arthritis encephalitis virus, Equine infectious anemia virus, Feline immunodeficiency virus, Human immunodeficiency virus 1, Human immunodeficiency virus 2; Orthomyxoviruses include but are not limited to: influenza viruses such as Alpha-influenzavirus, Beta-influenzavirus, Delta-influenzavirus, Gamma-influenzavirus;

In particular aspects, the viruses that are attenuated in this manner include but are not limited to: HIV-1, HIV-2, Influenza viruses, Hepatitis B virus (HBV), SARS-CoV-2, as well as isolates, clades, strains and mutants of these viruses, whether naturally occurring or not, including strains which have become resistant to art-known drug(s) (so-called drug or multidrug resistant strains). Recombinant forms of these viruses may also be used.

In some aspects, the virus that is used includes but is not limited to: DNA viruses such as Herpes viruses, Poxviruses, Hepadna viruses, Asfar viridae; RNA viruses such as Flavivirus, alphavirus, Togavirus, Coronavirus, Hepatitis D, Orthomyxovirus, Paramyxovirus, Rhabdovirus, Bunyavirus, Filovirus; Retroviruses such as human and animal Retroviruses; etc.

Live Attenuated Vaccines

The preparation of live attenuated viral vaccines typically requires the use of chemical or biological methods to modify and inactivate viral infectivity. In contrast, the present technology involves overexpressing members of the SHREK family of proteins in cells in which viruses are also simultaneously assembling. During viral assembly, one or more SHREK proteins are taken up and incorporated into the virions.

In some aspects, the present disclosure provides SHREK-overexpressing genetically engineered, recombinant cells for use in producing the attenuated viruses disclosed herein. In the cells, SHREK proteins are produced and present in an amount that is equal to or greater than the amount produced in a cell in nature, e.g. at least about 1 to about 100× more of the protein in present, such as about 1, 2, 5, 10, 20, 30, 40, 50, 60, 70, 80, 90 or 100 times more. A SHREK protein can be expressed in a cell that does not endogenously express the SHREK or a mutant version of the SHREK protein; and a SHREK protein or mutant version of the SHREK protein can also be over-expressed in a cell that normally expresses the SHREK. Such cells are generally genetically engineered, recombinant cells that are made using techniques known in the art. For example, heterologous genetic material such as DNA comprising at least one nucleic acid (polynucleotide) sequence (e.g. DNA, RNA, etc.) encoding a protein of interest such as a SHREK protein is introduced into the cells, e.g. by first being cloned into a DNA construct such as vector (e.g. an expression vector) comprising an expression cassette which includes the encoding nucleic acid. In the expression cassette, (and thus in the vector) the nucleic acid sequence is operably linked to genetic elements (e.g. a promoter) that permit expression of the protein. The vector is then introduced into suitable cells e.g. eukaryotic cells which can also act as a host for the virus, e.g. by transfection.

Similarly, genes encoding the viral genome (which includes at least nucleotide sequences encoding proteins and nucleic acids required for viral assembly) are cloned and introduced into cells using an expression vector as described above. In some aspects, the cells that are used to produce attenuated viruses comprise SHREK protein encoding genes and viral protein/nucleic acid encoding genes on separate expression vectors. In other aspects, SHREK protein encoding genes and viral protein/nucleic acid encoding genes are present on the same (i.e. on one or a single) expression vector.

A gene that is introduced into such a cell is typically referred to as a foreign or heterologous gene, i.e. a gene that is not found in the host cell in nature, and the encoded protein is also termed "foreign" or "heterologous" as it also is not found in the cell in nature, although this is not always the case. While the DNA sequence usually does not naturally occur in a host cell, some portions of the heterologous DNA sequence may occur in the host cell in nature (e.g. the portion that directly encodes a protein), but in nature other portions of the heterologous DNA are not present in the host cell, or at least not in association with that gene, e.g. in nature, the control elements (e.g. promoters) may differ, the location of the gene may differ (episomal or in a different location in the genomic DNA), and/or the copy number may differ, so that the amount of the proteins and nucleic acids that are expressed in the cell is greater than that which is found in nature. In some embodiments, a heterologous DNA sequence is a chimeric DNA sequence that is comprised of parts of different genes, including regulatory elements. Further, the amount and/or the specific amino acid sequence of an encoded protein may differ from that which is found in the host cell in nature.

The terms "polynucleotide" and "nucleic acid", used interchangeably herein, refer to a polymeric form of nucleotides of any length. These terms include, but are not limited to, a single stranded DNA, double-stranded DNA, genomic DNA, cDNA, or a polymer comprising purine and pyrimidine bases, or other natural, chemically, biochemically modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

As used herein, the term "promoter" refers to a nucleic acid sequence that functions to direct transcription of a downstream gene. In some embodiments, the promoter is appropriate to the host cell in which the target gene is being expressed. The promoter, together with other transcriptional and translational regulatory nucleic acid sequences (also termed "control sequences") drives expression of a gene or genes to which it is operably linked. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid. For example, a promoter or enhancer is operably linked to a coding sequence if it affects the transcription of the sequence; a ribosome binding site is operably linked to a coding sequence if it is positioned so as to facilitate translation; or a modified or heterologous pro region is operably linked to a mature region of a protein if it enables the processing of the full-length protein to produce the mature active form of the protein. Linkage may be contiguous or indirect.

As used herein, the terms "DNA construct" and "transforming DNA" may be used interchangeably to refer to DNA used to introduce sequences into a host cell. The DNA construct may be generated in vitro by PCR or any other suitable technique(s) known to those in the art. In some embodiments, the DNA construct comprises a sequence of interest (e.g., a sequence encoding a SHREK protein, and/or one or more sequence encoding viral proteins and genetic material). The DNA construct may further comprise a selectable marker. The DNA construct may comprise sequences homologous or non-homologous to the host cell chromosome. If homologous, the DNA construct may be used to mutagenize a region of the host cell chromosome i.e., by replacing an endogenous sequence with a heterologous sequence.

The term "expression cassette" refers to a nucleic acid construct generated recombinantly or synthetically, with a series of specified nucleic acid elements that permit transcription of a particular nucleic acid, such as a nucleic acid encoding a SHREK protein and/or viral proteins and/or viral genetic material, in a target cell.

The recombinant expression cassette can be incorporated into a vector such as a plasmid, chromosome, mitochondrial DNA, plastid DNA, virus, or nucleic acid fragment. Many prokaryotic and eukaryotic expression vectors are commercially available and selection of appropriate expression vectors and expression cassettes is within the knowledge of those of skill in the art. As used herein, the term "vector" refers to a polynucleotide construct designed to introduce nucleic acids into one or more cell types. Vectors include e.g. cloning vectors, expression vectors, shuttle vectors, and plasmids. As used herein, the term "plasmid" refers to a circular double-stranded (ds) DNA construct used as a cloning vector, and which forms an extrachromosomal self-replicating genetic element in some host cells or integrates into the host chromosome.

In alternative aspects, expression cassettes also include plasmids, expression vectors, recombinant viruses, any form of recombinant "naked DNA" vector, and the like. In alternative aspects, a "vector" can comprise a nucleic acid that can infect, transfect, transiently or permanently transduce a cell. In alternative aspects, a vector can be a naked nucleic acid, or a nucleic acid complexed with protein or lipid. In alternative aspects, vectors can comprise viral or bacterial nucleic acids and/or proteins, and/or membranes (e.g., a cell membrane, a viral lipid envelope, etc.). In alternative aspects, vectors can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879, the complete contents of which are hereby incorporated by reference in entirety), and can include both the expression and non-expression plasmids. In alternative aspects, a vector can be stably replicated by the cells during mitosis as an autonomous structure or can be incorporated within the host's genome.

Suitable promoters for use in the practice of the present methods include but are not limited to: all sequences capable of driving transcription of a coding sequence in a cell, e.g., a mammalian cell. Promoters used in the constructs provided herein include cis-acting transcriptional control elements and regulatory sequences that are involved in regulating or modulating the timing and/or rate of transcription of a nucleic acid, e.g., a SHREK-encoding nucleic acid. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

In alternative embodiments, "constitutive" promoters can be those that drive expression continuously under most environmental conditions and states of development or cell differentiation. In alternative embodiments, "inducible" or "regulatable" promoters can direct expression of a nucleic acid, e.g., a SHREK-encoding nucleic acid, under the influence of environmental conditions, administered chemical agents, or developmental conditions. Suitable vectors for use in the practice of the present methods include but are not limited to: plasmids, viral vectors, cosmids, and artificial chromosomes, etc. Of these, the most commonly used vectors are plasmids. Common to all engineered vectors are an origin of replication, a multicloning site, and a selectable marker.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication.

Promoters are discussed, for example, in published U.S. Pat. Nos. 10,729,788; 10,711,279; and 10,682,422, the complete contents of each of which are herein incorporated by reference in entirety.

In some aspects, the polynucleotide constructs encompassed herein comprise a DNA sequence encoding a full-length SHREK and/or viral protein and/or viral genetic material. In other aspects, the protein that is encoded comprises modifications when compared to the original sequence as found in nature, i.e. the protein is genetically engineered to contain one or more amino acid substitutions, which are generally conservative substitutions, one or more additions, or one or more deletions, e.g. amino or carboxy terminal truncations, as long as the changes do not change the ability of the protein to perform its intended function, i.e. to be incorporated into a virion and prevent the virion from being infective (for SHREK proteins) or to participate in virion assembly (for virus proteins). Similarly, the nucleic acid sequence that encodes the SHREK protein and/or the viral genetic material may be the same as that which is found in nature or may be genetically engineered or recombinant. It will be understood that, as a result of the degeneracy of the genetic code, many nucleotide sequences encoding a given protein may be produced.

Generally, the amino acid sequence of a disclosed protein or nucleic acid has at least about 75, 80, 85, 90, 95, 96, 97, 98 or 99% identity to the sequences disclosed herein, when assessed using standard techniques and algorithms known in the art.

As used herein, the term "introduced" refers to any method suitable for transferring nucleic acid sequences into the cell. Such methods include but are not limited to protoplast fusion, transfection, transformation, conjugation, and transduction (see e.g., Ferrari et al., "Genetics," in Hardwood et al., (eds.), *Bacillus*, Plenum Publishing Corp., pages 57-72, 1989). As used herein, the terms "transformed" and "stably transformed" refers to a cell that has a non-native (heterologous) polynucleotide sequence integrated into its genome or as e.g. an episomal element that is maintained for at least two generations.

A "host cell" refers to a suitable cell that serves as a host for an expression vector comprising DNA according to the present invention. A suitable host cell may be a naturally occurring or wild-type host cell, or it may be a genetically engineered host cell.

In some aspects, the host cells that are used to prepare attenuated viruses are eukaryotic cells. However, prokaryotic (microbial) cells that are transformed to overexpress one or more SHREK proteins and/or viral proteins and/or nucleic acids are also encompassed herein, whether or not they can also support virus assembly since they can be used for other purposes.

In some aspects, the host cells used to prepare attenuated viruses are capable of both 1) overexpression of one or more viable SHREK proteins, including appropriate glycosylation of the SHREK proteins; and 2) supporting transcription/translation of nucleic acid sequences encoding viral proteins and viral nucleic acids that are necessary for the production of virions (viruses, virus particles, etc.), and the assembly of those viral proteins and viral nucleic acids into virions. The viral genes may be introduced into the host cells in any suitable manner, e.g. the cells may be naturally susceptible to infection by the virus, or the viral genes may be introduced via the genetic engineering techniques discussed herein. One or more copies of the genes may be introduced into the cell.

As a caveat, if the virus is lentivirus, e.g. HIV, then the SHREK protein is not PSGL-1. In some aspects, if the virus is HIV, MVL or influenza, then the SHREK protein is not PSG-1 or CD43.

Suitable cells that can produce SHREK proteins and are amenable to the introduction of viral genes and subsequent viral replication include but are not limited to human cells or cell lines (which can be primary or immortalized), and include but are not limited to: HEK293T cells (derived from human fetal cells), A549 cells (derived from a cancer patient lung tumor), HeLa cells (a widely used human cell line isolated from cervical cancer patient Henrietta Lacks), Jurkat cells (a human T lymphocyte cell line isolated from a case of leukemia), keratinocytes and fibroblasts from various sources, cells from the National Cancer Institute's panel of human cell lines or the American Type Culture Collection (ATCC) depository, etc. as well as cells and cell lines available from many commercial sources.

The cell culture can be any type of cell culture, including adherent cell culture, e.g. cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable (see e.g. WO 2010/060719, and WO 2011/098592, both incorporated by reference herein, which describe suitable methods for obtaining and purifying large amounts of recombinant viruses). This can be accomplished by methods well known to persons skilled in the art and includes but is not limited to providing nutrients for the cell, for instance in the appropriate culture media. Suitable culture media are well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

In further aspects, what is provided is cell lines which overexpress at least one SHREK protein, the cell lines being suitable for infection by a virus that is to be attenuated or suitable for being genetically engineered by the incorporation of genetic material encoding viral proteins and nucleic acids capable of assembling into virions. The cells lines can be maintained (e.g. cultured, expanded, stored, preserved, etc.) and used when it is desired to produce attenuated viruses. Alternatively, or in addition, cell lines expressing or overexpressing genetic material encoding viral proteins and nucleic acids capable of assembling into virions are constructed and maintained; and/or cell lines encoding both i)

SHREK proteins and ii) viral proteins and nucleic acids capable of assembling into virions are constructed and maintained.

Compositions and Administration

Encompassed herein are pharmaceutical compositions (e.g. vaccines) comprising the antiviral agents disclosed herein. As used herein, "antiviral agent" refers to one the attenuated virions described herein and a pharmaceutically acceptable carrier or excipient. In generally, the attenuated virions are used as vaccines to prevent infection whereas the SHREK-antibody conjugates are used to treat an existing infection, although this is not always the case, as described elsewhere herein in the discussions of these two types of anti-viral agents.

The term "vaccine" implies that it is a pharmaceutical composition, and thus typically includes a pharmaceutically acceptable diluent, carrier or excipient. It may or may not comprise further active ingredients. In certain aspects, it may be a combination vaccine that further comprises other components that induce an immune response, e.g. against other proteins of the virus against which the composition is active, and/or against other infectious agents.

In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified virions are preferably formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The virions are typically in a solution having a suitable pharmaceutically acceptable buffer, and the solution may also contain various excipients such as, without limitation: stabilizing agents (e.g. albumin, etc.), solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavoring agents, coloring agents, administration aids, and combinations thereof. The compositions may also comprise pharmaceutically acceptable salts, examples of which include but are not limited to: sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts. etc. The compositions may be formulated into an injectable preparation. Such formulations contain effective amounts of the attenuated virions, and may be sterile liquid solutions, liquid suspensions or lyophilized versions, and may be aerosolized for intranasal administration.

In certain aspects, the compositions comprising the virions further comprise, or are administered together with, one or more adjuvants. Adjuvants are known in the art to further increase the immune response to an applied antigenic determinant. The terms "adjuvant" and "immune stimulant" are used interchangeably herein and are defined as one or more substances that cause stimulation of the immune system. In this context, an adjuvant is used to enhance an immune response to the virions present in the compositions. Examples of suitable adjuvants include but are not limited to: aluminum salts such as aluminum hydroxide, aluminum phosphate, aluminum potassium phosphate, or combinations thereof; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvants. Additional examples of adjuvants are listed in issued U.S. Pat. No. 10,730,915, the complete contents of which is herein incorporated by reference in entirety.

Prevention and/or Treatment of Diseases

Diseases and symptoms of diseases that are prevented and/or treated using one or more of the anti-viral agents that are described herein include any disease or symptom thereof caused by an enveloped virus. If the enveloped virus is a coronavirus, diseases/symptoms include but are not limited to: upper respiratory tract infections (URTIs) resembling the common cold, lower respiratory tract infections (LRTIs) such as bronchitis, pneumonia, and severe acute respiratory syndrome (SARS).

In some aspects, the compositions described herein are useful as vaccines and/or as preventive agents to elicit an immune response against the attenuated virions, such as an immune response to one or more components of the wild type virus that are present in the attenuated virions and accessible to cells of the immune system of a vaccinated subject. The term "vaccine" refers to an agent or composition containing an active component effective to induce a therapeutic degree of immunity in a subject against a certain pathogen or disease. For example, in some aspects, the vaccine comprises attenuated virions which, when administered to a subject, elicit an immune response against the attenuated virus. This provides a method of treating or preventing at least one symptom or complication that would otherwise occur due to infection with and/or replication of a wild-type, non-attenuated virus. The immune response may be protective, e.g. eliciting antibodies that neutralize non-attenuated viruses. A protective immune response may provide complete protection, i.e. completely preventing infection and the development of any symptoms of infection. However, those of skill in the art ill recognize that an immune response may be considered protection even if symptoms are not completely prevented but are lessened. For example, much benefit can accrue if the duration of an infection is decreased, or if the severity of one or more symptoms is limited or lessened, and/or if morbidity is decreased. For example, administration of the compositions can reduce the severity of subsequent disease by decreasing the length of disease, weight loss, severity of symptoms of the disease, decreasing the morbidity or mortality associated with the disease or reducing the likelihood of contracting the disease. The compositions may also reduce the spread of the pathogen by inhibiting transmission. The morbidity or mortality associated with the disease after administration of the vaccine vectors described herein may be reduced by 25%, 30%, 40%, 50%, 60%, 70%, 80%, 90% or even 100% as compared to similar subjects not provided the vaccine vector.

In other aspects, the antiviral agents disclosed herein, especially the SHREK-antibody conjugates, are used primarily or prophylactically to treat or prevent a viral infection and/or symptoms thereof. The infection may already have been acquired by the subject, i.e. the subject has been infected with the virus, as indicated by e.g. antibody tests and/or the detection of the agent (e.g. via a nasal or other swab) or by the detection of one or more symptoms of the infection, e.g. elevated temperature. For example, for SARS-COV-2, classical symptoms include Fever or chills, Cough, Shortness of breath or difficulty breathing, Fatigue, Muscle or body aches, Headache, New loss of taste or smell, Sore throat, Congestion or runny nose, Nausea or vomiting and/or Diarrhea; or for more serious cases, Trouble breathing, Persistent pain or pressure in the chest, New confusion, Inability to wake or stay awake and/or Bluish lips or face.

In other aspects, the subject that is treated may be suspected of having been exposed or likely to have been exposed to a virus. The subject may be, for example, a "front line" worker, a subject who has recently been in contact with an infected individual (e.g. for HIV, sexual contact is a risk factor), or has recently been in an environment known or likely to be harboring infectious particles, etc.

In some aspects, this technology is used to target latent HIV-1 reservoirs in a subject, rendering them no-longer capable of producing infectious virions. In this scenario, one or both of the vaccines and the antibody-SHREK conjugates may be used. Latent reservoirs may be present in a subject with an active, symptomatic infection or in a subject known or suspected to have been previously infected but is asymptomatic at the time of administration. The subject may be in a high-risk group that has a high probability of contracting the virus, or may be any naïve subject in whom it is desired to prevent future infections with the virus of interest, whether or not he/she is in or likely to be in a high-risk group.

The useful dosage of the antiviral agent to be administered may vary depending on the age, weight, species gender, ethnicity, etc. of the subject, the mode and route of administration and the type of pathogen against which an immune response is sought, and are best established by a skilled practitioner, such as a physician. The composition may be administered in any dose sufficient to evoke an immune response and may be administered once or as multiple doses ("booster" doses) administered e.g. several weeks, month or even years apart, depending on the duration of the immune response that is elicited. If a boosting vaccination is performed, typically such a boosting vaccination will be administered to the same subject at between one week and one year, preferably between two weeks and three, four or six months, after administering the composition to the subject for the first time (which is in such cases referred to as 'priming vaccination').

Administration of the compositions can be performed using any suitable standard route of administration. Non-limiting embodiments include parenteral administration, such as by injection e.g. intradermal, intramuscular, etc. or subcutaneous, transcutaneous, or mucosal administration, e.g. intranasal, oral, and the like; or by intranasal administration. In one aspect, a composition is administered by intramuscular injection, e.g. into the deltoid muscle of the arm, or vastus lateralis muscle of the thigh. The skilled person knows the various possibilities to administer a composition, e.g. a vaccine in order to induce an immune response to the antigen(s) in the vaccine.

Subjects to whom the compositions are administered are usually mammals and are frequently humans, and may be male, female, transgender, etc. However, veterinary applications of this technology are also encompassed, e.g. for non-human-primates, companion pets, various domesticated species, livestock, endangered species (even in the wild), animals in protected habitats, in breeding facilities and in zoos, etc. In some aspects, the subject is a feline, e.g. a cheetah, puma, jaguar, leopard, lion, lynx, tiger, or domestic cat. In some aspects, the subject is a human subject. The subject can be of any age, e.g. from about 1 month to 100 years old, e.g. from about 2 months to about 80 years old, e.g. from about 1 month to about 3 years old, from about 3 years to about 50 years old, from about 50 years to about 75 years old, etc.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of

EXAMPLES

Example 1. PSGL-1 Inhibits the Virion Incorporation of SARS-CoV and SARS-CoV-2 Spike Glycoproteins and Impairs Virus Attachment and Infectivity The ongoing COVID-19 global pandemic has afflicted more than 10 million people in over 200 countries and territories, resulting in more than 500,000 deaths as of Jun. 30, 2020. Currently, there are no effective treatments or vaccines. Understanding virus-host interactions is critical for developing novel therapeutics and vaccines.

The coronavirus spike (S) glycoproteins play an essential role in viral entry by binding the cell-surface receptor on target cells and mediating the fusion between viral and cellular membranes during virus entry. The S protein is also the target of neutralizing antibodies generated by the infected host. Because of its central role in virus infection and adaptive immunity, the S protein is a prime target for the development of antiviral therapeutics and vaccines. In addition to the adaptive arm of the host immune response, viral infections trigger an innate immune response, largely induced by IFN, that sets up an antiviral state. Hundreds of IFN-stimulated genes (ISGs) are induced by viral infection. While the role of some ISGs in blocking the replication of particular viruses has been well established, the vast majority of ISGs have not been characterized. Because of the significance of host innate immunity in viral transmission and replication within and between hosts, there is an unmet need to understand these antiviral inhibitory factors in detail.

To investigate the ability of PSGL-1 to restrict coronavirus infection, we first established a lentiviral vector-based coronavirus pseudovirus infection system, in which the S proteins from either SARS-CoV or SARS-CoV-2 were used to pseudotype lentiviral particles (FIG. 1A). Using this system, we assembled particles in the presence or absence of PSGL-1, and then used the particles to infect target Vero and Calu-3 cells, which endogenously express the primary SARS-CoV and CoV-2 receptor, angiotensin converting enzyme 2 (ACE2). The expression of PSGL-1 in viral producer cells had a minor (~ two-fold) effect on the release of SARS-CoV and -CoV-2 pseudovirions (FIGS. 1B and 1C). However, the infectivity of PSGL-1-imprinted SARS-CoV particles was completely abrogated in Vero cells (FIG. 1D), demonstrating the ability of PSGL-1 to block the infectivity of SARS-CoV S-bearing virion We further tested the effect of PSGL-1 on the infectivity of lentiviral particles pseudotyped with the SARS-Cov-2 S protein. We found that particles pseudotyped with SARS-CoV-2 S protein had much lower infectivity than those pseudotyped with SARS-CoV S protein. To resolve this technical issue, we developed a more sensitive reporter system in which a luciferase reporter (Luc) gene was expressed from the HIV-1 LTR in the presence of co-expressed HIV-1 Tat protein (FIG. 1A). A major advantage of this system is that high-level Luc expression can be achieved upon transactivation by co-expressed Tat protein following viral entry, which minimizes non-specific Luc background from non-productive viral entry. Using this system, we found that the infectivity of the SARS-CoV-2 pseudovirus is also potently inhibited by the expression of PSGL-1 in the virus-producer cells (FIGS. 1E and 1F). Together, these results demonstrate that PSGL-1 expression in the virus-producer cells severely diminishes the infectivity of virions bearing SARS coronavirus S proteins.

To investigate possible mechanisms, we analyzed the virion incorporation of SARS-CoV S proteins in the presence of PSGL-1. As shown in FIG. 2B, the expression of PSGL-1 in the virus-producer cell decreased the amount of both SARS-CoV and SARS-CoV-2 S proteins on virions. We performed a virion attachment assay and observed that the lentiviral particles pseudotyped with SARS-CoV or SARS-CoV-2 S protein produced from PSGL-1-expressing cells were impaired in their ability to attach to target cells (FIG. 2D). These results demonstrate that the presence of PSGL-1 on virus particles can structurally hinder virion interaction with the target cells even in the presence of remaining S proteins.

In this report, we demonstrate that the expression of PSGL-1 in virus-producer cells impairs the infectivity of virions bearing the S protein of either SARS-CoV or SARS-CoV-2, a phenotype shared among several other viruses (e.g., HIV-1, murine leukemia virus, and influenza virus). The expression of PSGL-1 in virus-producing cells impairs the incorporation of SARS-CoV and SARS-CoV-2 spike (S) glycoproteins into pseudovirions and blocks virus attachment and infection of target cells.

Materials and Methods

Virus assembly. The SARS-CoV S and SARS-CoV-2 S expression vectors were gifts. Pseudoviruses were assembled by cotransfection with SARS-CoV-S or -CoV-2 S expression vector (0.5 μg), pCMVΔR8.2 (7.5 μg), and pLKO.1-puro-TurboGFP (10 μg) or pLTR-Tat-IRES-Luc (10 μg), with either pCMV3-PSGL-1 (2 μg) or pCMV3-Empty vector (2 μg) as previously described (Fu Y, et al. (2020) Proc Natl Acad Sci USA 117(17):9537-9545.). Virus supernatants were collected at 48-84 hours and concentrated by ultracentrifugation.

Viral infectivity assay. Virus particles produced in the presence of PSGL-1 were used to infect Vero E6 or Calu-3 cells (ATCC). Cells were pretreated with CoV-2 Pseudovirus Infection Enhancer (CoV-2 PIE) for 1 hour at 37° C., and then infected for 5 hours. Infected cells were cultured for 3 days. Cells were lysed in Luciferase Assay Lysis Buffer and quantified by using GloMax® Discover Microplate Reader (Promega).

Virion incorporation of SARS-CoV S proteins. HEK293T cells were co-transfected with HIV-1 Env-defective pNL4-3/KFS (1 μg) and vectors expressing the S protein of either SARS-CoV or SARS-CoV-2 (100 ng) in the presence of PSGL-1 expression vector or an empty control vector (200 ng). Virions were analyzed by SDS-PAGE and western blot using antibodies against SARS-CoV spike proteins (Genetex), PSGL-1 (KPL-1 clone), or HIV-Ig to detect CA protein p24.

Viral attachment assay. Virus particles were incubated with Vero E6 cells (pre-chilled at 4° C. for 1 hour) at 4° C. for 2 hours. The cells were then washed extensively with cold PBS buffer for 5 times, and then lysed in NuPAGE™ LDS Sample Buffer (Invitrogen). Cell lysates were analyzed by SDS-PAGE and western blotting.

Example 2. Identification of the SHREK Family of Proteins for Inactivating HIV-1, Influenza A, and SARS-CoV-2

Currently, there are approximately 37 million people living with HIV, with about 1.8 million new cases of HIV globally and 940,000 HIV-related deaths in 2017. Despite substantial effort in HIV research, an effective vaccine remains elusive. Significant medical progress has been made in combating HIV infection, transmission, and disease progression by the development of antiretroviral therapy (ART) drugs. These antiviral drugs can significantly improve outcomes for people who are already infected with HIV. However, ART must be taken for the entire lifetime of the affected patients to keep viral replication levels below detectable levels. In addition, antiretroviral therapy does not eliminate a population of cells known as latent HIV reservoirs. These cells are infected with HIV but are not actively producing new virions. However, they can later become active again and start making more HIV. Latent reservoir cells are the major hurdle that stands in the way of finding an HIV cure. Thus, investigating the molecular details of HIV replication, immune evasion, and virus-host interactions is essential for the identification of new strategies that can eliminate or deactivate HIV latent reservoirs.

Previous studies have demonstrated that steric hindrance is a major mechanism of PSGL-1 restriction of HIV-1 infectivity. The extracellular domain of PSGL-1 is necessary for its antiviral activity, and deletion of the highly glycosylated extracellular decameric repeats diminishes the ability of PSGL-1 to inactivate HIV-1 infectivity. This example describes tests of whether molecules with a structure similar to that of PSGL-1 would block HIV-1 virion infectivity. A group of cellular proteins, including CD43, TIM-1, CD34, PODXL1, PODXL2, CD164, MUC1, MUC4, and TMEM123 (FIG. 3A), have diverse coding sequences, tissue expression patterns, and functionalities, but share a similar structural feature, namely a highly extended and heavily glycosylated extracellular domain. CD43 is a sialomucin transmembrane protein expressed at high levels on T lymphocytes, monocytes, and some B lymphocytes. TIM-1 is preferentially expressed on Th2 T cells, and also contains an extracellular mucin domain and an N-terminal immunoglobulin (Ig)-like domain. CD34, the common surface marker of stem and progenitor cells, is also a member of the sialomucin family of proteins, which contain an extensively O-glycosylated extracellular mucin-like domain. The podocalyxin-like proteins 1 and 2 (PODXL1 and PODXL2) are CD34-related sialomucins and share a similar structure with CD34 and are also markers of hematopoietic stem and progenitor cells. CD164 is another sialomucin co-expressed with CD34 on the surface of human hematopoietic cells and is structurally similar to CD34. Two mucins, MUC1 and MUC4, which are transmembrane mucins with dense arrays of O-linked oligosaccharides attached to the threonine and serine residues in extracellular domains, were also investigated. TMEM123 (Porimin) is another mucin-like protein with high contents of glycosylated threonine and serine residues in its extracellular domain.

To determine whether these proteins have antiviral activity, we cotransfected them individually with HIV-1(NL4-3) DNA into HEK293T cells to assemble viral particles. The release of virions in the presence of these proteins was first quantified. All of the proteins except TIM-1 had minor effects on virion release at doses below 100 ng (FIG. 3B). We further quantified the infectivity of virions by using an equal p24 level of virus particles to infect an HIV-1 Rev-dependent indicator cell, Rev-A3R5-GFP. The presence of each of these proteins in virus producer cells blocked the infectivity of the virions released (FIG. 1B 3B) in a dosage-dependent manner (FIGS. 1C 3C). The 50% inhibition dosages were further quantified (FIG. 4D and FIG. 8A-G). Among these proteins, CD34, the common stem cell maker, had the most potent anti-HIV activity, blocking HIV-1 virion infectivity at an $IC_{50}$ of 2.33 ng (FIG. 4E); MUC1 was the least potent, with an $IC_{50}$ of 216.06 ng (FIG. 4E. Based on the antiviral activities and shared structural feature of these proteins, we conveniently named them the Surface-Hinged, Rigidly-Extended Killer (SHREK) family of virion inactivators.

We performed a virion attachment assay using particles produced from cells expressing each individual SHREK protein. As shown in FIG. 5A, as a control, particles produced from the PSGL-1-expressing cells were highly impaired in their ability to attach to target cells. Similar strong impairment was observed for virions produced from the CD34- and the PODXL2-expressing cells. Of note, these three proteins (PSGL-1, CD34, and PODXL2) are also the most potent virion inactivators among SHREKs, with an $IC_{50}$ around 2 ng (FIG. 4E). The other proteins (CD43, CD164, PODXL1, MUC1, and MUC4) also inhibited virion attachment to varying degrees. Interestingly, TMEM123 slightly enhanced HIV-1 virion attachment to target cells, although it inhibited viral infection (Figure and E 4D and 4E). One possible reason is that TMEM123 itself may interact with surface proteins, thereby promoting non-productive attachment of virus particles to target cells. Indeed, when the binding assay was performed in the presence of an anti-TMEM123 antibody to block possible TMEM123 interaction with cell surface proteins, the enhancement of viral binding was diminished, and virion attachment was decreased (FIG. 5B).

To further determine whether these SHREK proteins also possess broad-spectrum antiviral activity, we tested their ability to block other viruses, including influenza A and SARS-CoV-2 pseudoviruses. To assemble influenza A virus, eight vectors expressing each of the segments of the influenza A/WSN/33 (H1N1) genome plus a GFP-reporter vector were cotransfected with individual SHREK proteins into HEK293T (FIG. 6A). Viral particles were harvested and used to infect target MDCK cells. As shown in FIG. 6B, the presence of each of the SHREK proteins in virus-producer cells inhibited the infection of target cells by the virions that were released. However, the degree of inhibition was different; MUC1, PDOXL1, and MUC4 had the strongest inhibition of influenza A virus, although MUC1 and MUC4 were less effective against HIV-1. CD164 and TMEM123 had the weakest inhibition of influenza A. These results demonstrate that SHREK proteins are broad-spectrum and can block the infectivity of multiple viruses. In addition, for each individual SHREK, its antiviral potency can vary among different viruses, with the differences likely related to possible viral antagonisms and other unidentified factors.

To test the effects of SHREK on SARS-CoV-2 infection, we assembled lenti-based SARS-CoV-2 S protein pseudoviruses in the presence of individual SHREKs, using PSGL-1 as a control. We performed similar experiments on all the SHREKs and found that all except MUC1 inhibited the infection of SARS-CoV-2 pseudoviruses (FIG. 6C); PSGL-1, CD34, CD164, and MUC4 had the strongest inhibition among SHREKs.

In this report, we identified a group of proteins, namely SHREKs, that share similar structural characteristics and the ability to broadly inactivate virion infectivity. We also quantified their anti-HIV activity using a range of doses (from 0.5 ng to 400 ng of SHREK expression vector) and observed a strictly dosage-dependent inhibition of virion infectivity (FIG. 4). Although we only tested proteins with mucin and mucin-like domains, we expect that SHREK proteins will likely include other proteins with diverse molecular structures that can block viral infection. Without being bound by theory, it is believed that the antiviral activities of SHREK are achieved through at least 3 different mechanisms: (1) blocking virion release (e.g. TIM-1 inhibition of HIV-1 release); (2) inhibition of virion incorporation of viral attachment proteins (e.g. PSGL-1 inhibition of HIV-1 gp160 incorporation); (3) virion incorporation of SHREK that blocks progeny virus attachment to target cells through steric hindrance (e.g. PSGL-1 inhibition of HIV-1 virus attachment to target cells).

We found that all SHREKs except MUC1 inhibited SARS-CoV-2 pseudoviruses. MUC1 and MUC4 are closely related mucins. The differential inhibition of SARS-CoV-2 by MUC4 but not MUC1 is not currently understood and may relate to possible antagonism for MUC1 from the SARS-CoV-2 S protein.

Our identification of the SHREK family of proteins offers potential new antiviral therapeutics that may be developed through the induction and modulation of SHREK activities and the inhibition of viral antagonisms.

Methods

Cells and Cell Culture

HEK293T (ATCC), MDCK (ATCC), Calu-3 (ATCC), and HeLaJC.53 (a gift) were maintained in Dulbecco's modified Eagle's medium (DMEM) (Invitrogen) containing 10% heat-inactivated FBS and 1× penicillin-streptomycin (Invitrogen). HIV Rev-dependent GFP indicator Rev-A3R5-GFP cells (Virongy) were cultured in RPMI-1640 plus 10% FBS supplemented with 1 μg/ml geneticin (G418) (Sigma-Aldrich) and 1 μg/ml puromycin (Sigma-Aldrich).

Plasmid Transfection and Virus Production

The infectious HIV-1 molecular clone pHIV-1(NL4-3) was obtained from the NIH AIDS Reagent Program. pCMV3-PSGL-1, pCMV3-CD43, pCMV3-CD164, pCMV3-TMEM123, pCMV3-CD34, pCMV3-PODXL1, pCMV3-PODXL2, pCMV3-TIM1, pCMV3-MUC1, pCMV3-MUC4, pCMV3-Empty, and SARS-CoV-2 S protein expression vector were purchased from Sinobiological. The pHW-NA-GFP (ΔAT6) Reporter plasmid and the A/WSN/1933 H1N1-derived plasmids pHW2000-PB2, pHW2000-PB1, pHW2000-PA, pHW2000-HA, pHW2000-NP, pHW2000-NA, pHW2000-M, and pHW2000-NS were a gift. pLTR-Tat-IRES-Luc was previously described (Meltzer, B. et al. Virology 518, 241-252, doi:10.1016/j.virol.2018.03.006 (2018)). For HIV-1 viral production, HEK293T cells were cotransfected in a 6-well plate with 1 μg of pHIV-1(NL4-3) plus the indicated doses of pCMV3-CD164, pCMV3-TMEM123, pCMV3-CD34, pCMV3-PODXL1, pCMV3-PODXL2, pCMV3-TIM1, pCMV3-MUC1, pCMV3-MUC4 and pCMV3-Empty. Supernatants were collected at 48 hours post transfection. For influenza A-GFP reporter particle assembly, HEK293T cells were cotransfected with pHW2000-PB2, pHW2000-PB1, pHW2000-PA, pHW2000-HA, pHW2000-NP, pHW2000-NA, pHW2000-M, and pHW2000-NS (0.25 μg each); pHW-NA-G (ΔAT6) (L5 μg); and pCMV3-PSGL-1, pCMV3-CD43, pCMV3-CD164, pCMV3-TMEM123, pCMV3-CD34, pCMV3-PODXL1, pCMV3-PODXL2, pCMV3-TIM1, pCMV3-MUC1, pCMV3-MUC4, or pCMV3-Empty DNA (0.5 μg each) in a 6-well plate. Viral supernatants were harvested at 48 hours. For SARS-CoV-2-S-pseudotyped lentiviral particle production, HEK293T cells were cotransfected in 10-cm dishes with pLTR-Tat-IRES-Luc (10 μg), pCMVΔR8.2 (7 μg), SARS-CoV-2 S (1 μg), and pCMV3-PSGL-1, pCMV3-MUC1, pCMV3-MUC4, or pCMV3-Empty DNA (2 μg each). Supernatants were harvested at 48 and 72 hours and concentrated using gradient centrifugation.

Virus Infectivity Assays

For the HIV-1 infectivity assay, p24-normalized HIV-1 particles produced in the presence of PSGL-1, CD43, CD164, TMEM123, CD34, PODXL1, PODXL2, TIM1, MUC1, MUC4, or empty vector were used to infect Rev-A3R5-GFP cells (0.2 to 0.5 million cells per infection). The percentage of GFP+ cells was quantified by flow cytometry at 48 or 72 hours post infection. The IC50 inhibition curves were generated using GraphPad Software, La Jolla, California, USA. For the influenza A virion infectivity assay, influenza A-GFP reporter viruses were assembled in the presence of PSGL-1, CD43, CD164, TMEM123, CD34, PODXL1, PODXL2, TIM1, MUC1, MUC4, or empty vectors. Virions were harvested at 48 hours and used to infect MDCK cells ($3\times10^4$ cells per infection). GFP expression was quantified at 24 hours post infection by flow cytometry. For the SARS-CoV-2-S-pseudotyped lentivirus infectivity assay, Calu-3 cells (0.5 million cells per infection) were pre-treated with CoV-2 PIE (Virongy) for 1 hour at 37° C. and then infected with equal p24 inocula of SARS-CoV-2-S-pseudotyped luciferase reporter lentiviruses. Cells were lysed at 72 hours post infection using Luciferase Assay Lysis Buffer (Promega). Luminescence was measured on a GloMax® Discover Microplate Reader (Promega).

Viral Attachment Assay

HIV-1 virus particles produced in the presence of PSGL-1, CD43, CD164, TMEM123, CD34, PODXL1, PODXL2, TIM-1, MUC1, MUC4, or empty vector were incubated with HelaJC.53 cells (prechilled at 4° C. for 1 h) at 4° C. for 2 h. The cells were then washed extensively (5 times) with cold PBS buffer and then lysed with LDS lysis buffer (Invitrogen) for analysis by Western blot. The attachment of HIV-1 virus produced in the presence of TMEM123 was also separately tested by pre-incubating the virus with mouse monoclonal anti-TMEM123 antibody (297617) (ThermoFisher) (25 ug/ml) at 37° C. for 1 h, followed by incubation of the virus with HeLaJC.53 cells at 4° C. for 2 h and lysing with LDS buffer.

Western Blots

Cells were lysed in LDS lysis buffer (Invitrogen). Proteins were denatured by boiling in sample buffer and subjected to SDS-PAGE, transferred to nitrocellulose membrane, and incubated overnight at 4° C. with one of the following primary antibodies: mouse anti-HIV-1 p24 monoclonal antibody (183-H12-5C) (NIH AIDS Reagent Program) (1:1000 dilution), mouse anti-MUC1 antibody (HMPV) (BD Biosciences) (1:1000 dilution), mouse monoclonal anti-MUC4 antibody (1G8) (ThermoFisher) (1:1000 dilution), mouse monoclonal anti-TMEM123 antibody (297617) (ThermoFisher) (1:1000 dilution), or anti-GAPDH goat polyclonal antibody (Abcam) (1:1000 dilution). Membranes were incubated with HRP-labeled goat anti-mouse IgG (KPL) (1:2500 dilution) for 60 min at room temperature. Chemiluminescence signal was detected by using West Femto chemiluminescence substrate (Thermo Fisher Scientific), and images were captured with a CCD camera (FluorChem™ 9900 Imaging Systems) (Alpha Innotech).

p24 ELISA

Detection of extracellular HIV-1 p24 and quantification of HIV-1 or SARS-CoV-2-S-pseudotyped lentivirus particles were performed using an in-house p24 ELISA kit. Briefly, microtiter plates (Sigma-Aldrich) were coated with anti-HIV-1 p24 monoclonal antibody (183-H12-5C) (NIH AIDS Reagent Program). Samples were incubated for 2 hours at 37° C., followed by washing and incubating with biotinylated anti-HIV immune globulin (HIVIG) (NIH AIDS Reagent Program) for 1 hour at 37° C. Plates were then washed and incubated with avidin-peroxidase conjugate (R &D Systems) for 1 hour at 37° C., followed by washing and incubating with tetramethylbenzidine (TMB) substrate. Plates were kinetically read using an EL×808™ automatic microplate reader (Bio-Tek Instruments) at 630 nm.

Surface Staining

HEK293T cells were transfected with 400 ng of pCMV3-PSGL-1, pCMV3-CD43, pCMV3-CD164, pCMV3-CD34, pCMV3-PODXL1, pCMV3-PODXL2, pCMV3-TIM1, or pCMV3-Empty DNA. At 48 hours post transfection, 0.5-1 million cells were stained with one of the following primary antibodies: mouse anti-PSGL1 antibody (KPL-1) (BD Pharmingen), mouse anti-CD43 antibody (1G10) (BD Biosciences), mouse anti-CD164 antibody (67D2) (Biolegend), mouse anti-CD34 antibody (563) (BD Biosciences), mouse anti-TIM1 antibody (219211) (R & D Systems), mouse monoclonal anti-PODXL1 antibody (222328) (R & D systems), or mouse monoclonal anti-PODXL2 antibody (211816) (R & D Systems), followed by staining with Alexa Fluor® 488-conjugated goat anti-mouse secondary antibody (Invitrogen).

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A recombinant host cell comprising one or more vectors comprising heterologous nucleic acid sequences encoding one or more Surface-Hinged, Rigidly-Extended Killer (SHREK) proteins selected from the group consisting of CD43, TMEM123, CD164, Tim-1, CD34, PODXL2, CD45, CD44, Madcam1, glycam1, Cd68, CD148, CX3CL1, CD107a, CD99, and CD7, and a viral genome selected from the group consisting of coronavirus, a lentivirus, a hepadnavirus, and an influenza virus.

2. The host cell of claim 1, wherein the host cell is a mammalian cell.

3. The recombinant host cell of claim 1 wherein the viral genome is a lentivirus.

4. The recombinant host cell of claim 3 wherein the lentivirus is HIV-1.

5. The recombinant host cell of claim 1 wherein the viral genome is a coronavirus.

6. The recombinant host cell of claim 5 wherein the coronavirus is SARS-CoV-2.

7. The recombinant host cell of claim 1 wherein the viral genome is a hepadnavirus.

8. The recombinant host cell of claim 7 wherein the hepadnavirus is HBV.

9. A method of producing virions, comprising

I) introducing into a host cell a nucleic acid sequence encoding at least one Surface-Hinged, Rigidly-Extended Killer (SHREK) protein, wherein the at least one SHREK protein is selected from the group consisting of CD43, TMEM123, CD164, Tim-1, CD34, PODXL2, CD45, CD44, Madcam1, glycam1, Cd68, CD148, CX3CL1, CD107a, CD99, and CD7, and one or more nucleic acid sequences encoding a viral genome;

II) culturing the host cell in a culture medium under conditions that permit i) over-expression of the SHREK protein from the nucleic acid sequence and over-expression of viral proteins and viral nucleic acids from the one or more nucleic acid sequences, and ii) assembly of the viral proteins and viral nucleic acids into virions comprising the SHREK protein; and III) recovering the virions from the culture medium.

10. The method of claim 9 wherein the host cell is a mammalian cell.

11. The method of claim 9 wherein the viral genome is selected from the group consisting of coronavirus, a lentivirus, a hepadnavirus, and an influenza virus.

12. The method of claim 11 wherein the viral genome is a lentivirus.

13. The method of claim 12 wherein the lentivirus is HIV-1.

* * * * *